United States Patent [19]

Banchereau et al.

[11] Patent Number: 6,004,807
[45] Date of Patent: Dec. 21, 1999

[54] IN VITRO GENERATION OF HUMAN DENDRITIC CELLS

[75] Inventors: Jacques Banchereau, Ecully; Christophe Caux, Lyons, both of France

[73] Assignee: Schering Corporation, Kenilworth, N.J.

[21] Appl. No.: 08/637,880

[22] Filed: Apr. 25, 1996

Related U.S. Application Data

[62] Division of application No. 08/331,531, Sep. 26, 1994, abandoned.

[30] Foreign Application Priority Data

Mar. 30, 1992 [EP]  European Pat. Off. .............. 92400879

[51] Int. Cl.$^6$ ................................................... C12N 5/00
[52] U.S. Cl. ......................... 435/325; 435/347; 435/373; 435/326
[58] Field of Search .................................... 435/325, 347, 435/373, 326

[56] References Cited

U.S. PATENT DOCUMENTS

| | | |
|---|---|---|
| 4,677,063 | 6/1987 | Mark et al. . |
| 4,959,455 | 9/1990 | Clark et al. . |
| 5,128,259 | 7/1992 | Morgan et al. . |

FOREIGN PATENT DOCUMENTS

| | | |
|---|---|---|
| 0 455 482 | 11/1991 | European Pat. Off. . |
| WO86/00639 | 1/1986 | WIPO . |
| WO91/02531 | 3/1991 | WIPO . |
| WO91/06630 | 5/1991 | WIPO . |
| WO91/13632 | 9/1991 | WIPO . |
| WO93/04187 | 3/1993 | WIPO . |
| WO93/20185 | 10/1993 | WIPO . |
| WO94/02156 | 2/1994 | WIPO . |
| WO94/05323 | 3/1994 | WIPO . |

OTHER PUBLICATIONS

Aggarwal et al., J. Biol. Chem., 260:2345–2354 (1985).
Banchereau et al., Science, 251:70–72 (1991).
Belsito et al., New Eng. J. Med., 310:1279–1282 (1984).
Carswell et al., Proc. Nat. Acad. Sci. USA. 72:3666–3670 (1975).
Caux et al., Blood, 75:2292–2298 (1990).
Celis et al., Proc. Natl. Acad. Sci. USA, 91:2105–2109 (1994).
Celluzzi et al., J. Exp. Med., 183:283–287 (1996).
Dubey et al., Immunogenetics and Transplantation Immunology, Chap. 131, pp. 847–858 In: Rose et al. eds., Manual of Clinical Laboratory Immunology 3d Edition (Am. Soc. Microbiol.) (1986).
Duchosal et al., Nature, 355:258–262 (1992).
Freudenthal et al., Proc. Natl. Acad. USA, 87:7698–7702 (1990).
Hsieh et al., J. Cell. Biochem. Suppl., 21A:11 Abstr. C1–110 (1995).
Hsu et al., Nature, 2:52–58 (1996).
Knight et al., Immunol. Lett., 19:177–182 (1988).
Macatonia et al., Immunology, 71:38–45 (1990).
Macatonia et al., Immunology, 74:399–406 (1991).
Mandelboim et al., Nature Medicine, 1:1179–1183 (1995).
Mayordomo et al., Nature Medicine, 1:1297–1302(1995).
Mosier et al., Current Topics in Microbiology and Immunology, 152:195–199 (1989).
Moulon et al. J. Invest. Derm., 97:524–528 (1991).
Mukherji et al., Proc. Natl. Acad. Sci. USA, 92:8078–8082 (1995).
Nair et al., J. Exp. Med., 175:609–612 (1992).
Nishimura et al., Embase Database Abstr. No. 91344512 (Abstr. of Jpn. J. Cancer Res., 82:1207–1210 (1991).
Nonacs et al., J. Exp. Med., 176:519–529 (1992).
Paglia et al., J. Exp. Med., 183:317–322 (1996).
Patterson et al., J. Gen Virol., 68:1177–1181 (1987).
Peters et al., In Dendritic Cells in Fundamental and Clinical Immunology, Kampordijk et al., Plenum Press, New York (1993).
Porcelli et al., Nature, 360:593–596 (1992).
Reid et al., Blood, 76:1139–1149 (1990).
Reid et al., J. Immunol., 149:2681–2688 (1992).
Romani et al., J. Exp. Med., 180:83–93 (1994).
Sallusto et al., J. Exp. Med., 179:1109–1118 (1994).
Santiago–Schwarz et al., J. of Leukocyte Biol., 52:274–281 (1992).
Seman et al., Europ. J. Immunol., 20:1265–1272 (1990).
Sornasse et al., J. Exp. Med., 175:15–21 (1992).
Steinman, Annuv. Rev. Immunol., 9:271–296 (1991).
Steinman et al., Phagocytes, Chap. 49, pp. 49.1–49.9 In: Herzenberg et al., eds. Cellular Immunology, vol. 2 (Blackwell Scientific Publications, Oxford) (1986).
Strominger, Nature, 1:1140 (1995).
Teunissen et al., J. Invest Derm., 94:166–173 (1990).
Tschacler et al., J. Invest. Derm., 88:233–237 (1987).
van der Bruggen et al., Science, 254:1643–1647 (1991).
Young et al., J. Exp. Med., 171:1315–1332 (1991).
Young et al., J. Exp. Med., 183:7–11 (1996).
Zitvogel et al., J. Exp. Med., 183:87–97 (1996).

*Primary Examiner*—Leon B. Lankford, Jr.
*Attorney, Agent, or Firm*—Cynthia L. Foulke

[57] ABSTRACT

A method is provided for generating human dendritic cells in vitro by treating CD34$^+$ cells with tumor necrosis factor-$\alpha$ and interleukin-3 or with GM-CSF. The invention also includes cellular compositions of dendritic cells produced by this method. Dendritic cells of the invention can be used widely as components in many diagnostic and therapeutic systems, including improved mixed lymphocyte reactions for assaying tissue rejection, adoptive immunotherapy of cancer, adoptive immunotherapy of HIV and other viral infections, and SCID-hu mice for human antibody production.

6 Claims, 7 Drawing Sheets

IN VITRO GENERATION OF HUMAN DENDRITIC CELLS

This is a division of U.S. application Ser. No. 331,531, filed Sep. 26, 1994 now abandoned.

The invention relates generally to an in vitro method of generating human dendritic cells, and, more specifically, to therapeutic and diagnostic uses of the generated cells.

Dendritic cells are a system of antigen-presenting cells that function to initiate several immune responses such as the sensitization of MHC-restricted T cells, the rejection of organ transplants, and the formation of T cell-dependent antibodies. Dendritic cells are found in many nonlymphoid tissues but can migrate via the afferent lymph or the blood stream to the T cell-dependent areas of lymphoid organs. They are found in the skin, where they are named Langerhans cells, and are also present in the mucosa. They represent the sentinels of the immune system within the peripheral tissues where they can acquire antigens. As these cells express CD4 and can be infected in vitro by HIV, they are likely to present a port of entry of virus in vivo: e.g. Knight et al., pp. 145 in Racz, et al., editors, "Accessory Cells in HIV and Other Retroviral Infections" (Karger, Basel, 1991); Ramsauer et al., pp. 155 in Racz, et al., editors (cited above). The isolation of human dendritic cells from peripheral blood has only recently been achieved and only small numbers of cells can be generated, e.g. Freudenthal et al., Proc. Natl. Acad. Sci., Vol. 87, pp. 7698 (1990). The in vitro generation of large numbers of human dendritic cells would present an important advantage for priming in vitro human naive CD4 and CD8 T cells, for screening agents that may interfere with HIV infection, for generating primary and secondary in vivo response of human B cells in SCID-hu mice reconstituted with human T and B cells, and for constructing a more sensitive mixed-lymphocyte reaction assay.

A major impediment to transplantation of allogeneic tissue and organs is graft rejection by the transplant recipient. The cell-mediated immune reaction of the recipient, or host, to the donor tissue plays an important role in the rejection process. The cell-mediated immune response has two important phases: (i) recognition, when host cells recognize the donor cell as foreign in the context of the major histocompatibility complex (MHC); and (ii) destruction, when the host cells respond by attacking the foreign cells. As part of the attacking process, a number of responder cells undergo proliferation and acquire cytotoxicity—that is, the ability to kill donor cells displaying the appropriate antigens. Thus, cell-mediated immunity can be described in terms of two measurable functions: proliferation, and cytotoxic activity—see Dubey et al., chapter 131 in Rose et al., Editors, "Manual of Clinical Laboratory Immunology", 3rd edition (American Society of Microbiology, Washington, D.C., 1986).

Development of cell culture techniques has led to the establishment of in vitro methods that mimic the in vivo immunization process, thus providing measures for the assessment of cell-mediated immunity in vitro. Of particular utility in regard to transplantation is the mixed lymphocyte response (MLR), or mixed lymphocyte culture. The MLR is a relatively simple assay, yet it exists in many variants. Typically, the assay consists of mixing responder lymphocytes in a suitable culture system with stimulator lymphocytes whose proliferation and/or transcription machinery has been disabled, e.g. by irradiation. After the cells have been cultured for several days, a number of different measurements can be made to quantify the degree of reactivity of the responder cells to the stimulator cells, e.g. uptake of tritiated thymidine, number of blast cells, number of dividing cells, cytokine production, and the like. Other variables in the assay include the source of the responder and stimulator cells, e.g. peripheral blood, spleen, lymph nodes, etc.; whether the responder cells are syngeneic, allogeneic, or xenogenic with respect to the stimulator cells; the method of disabling the stimulator cells, for example irradiation or treatment with a DNA synthesis inhibitor (e.g. mitomycin C) or the like.

A drawback of the MLR as a routine assay for cell-mediated immune reactivity is sensitivity. Frequently, it is difficult to obtain a strong effect in the MLR, whatever the particular read-out employed. It is believed that antigen-presenting cells in the stimulator population are responsible for stimulating the responder cells; however, in most tissue sources such cells are few in number and/or are of a type that stimulates inefficiently. The sensitivity, and hence the utility, of the MLR assay could be greatly enhanced by the availability of more potent stimulator cell populations. Dendritic cells could serve this function, since they are well known as potent antigen-presenting cells, e.g. Steinman, *Ann. Rev. Immunol.*, Vol. 9, pgs. 271–296 (1991). Unfortunately, it is presently very difficult to obtain them in quantities sufficient for routine MLRs, e.g. Steinman, et al., chapter 49 in Herzenberg et al., Editors, "Cellular Immunology" Vol. 2 (Blackwell Scientific Publications, Oxford, 1986).

SUMMARY OF THE INVENTION

The invention is directed to a method for in vitro generation of human dendritic cells. The invention also includes isolated populations of human dendritic cells produced by the method of the invention and applications of the isolated cells, including an improved MLR assay that employs a pure population of dendritic cells as stimulator cells. The method of the invention includes the steps of culturing $CD34^+$ hematopoietic progenitor cells in the presence of tumor necrosis factor-$\alpha$ (TNF-$\alpha$) and interleukin-3 (IL-3) or of granulocyte-macrophage colony stimulating factor (GM-CSF) to form $CD1a^+$ dendritic cells of the invention.

The invention therefore provides a process for the preparation of a cellular composition comprising human dendritic cells, comprising the steps of:

treating $CD34^+$ hematopoietic cells with TNF-$\alpha$ and IL-3 or with GM-CSF;

and isolating the treated $CD34^+$ hematopoietic cells that express the CD1a antigen.

Preferably the $CD34^+$ cells are treated with TNF-$\alpha$ in addition to GM-CSF.

The invention also provides $CD34^+$ hematopoietic cells that express the CD1a antigen following in vitro culture; and a cellular composition comprising human dendritic cells produced by the process defined above.

Dendritic cells initiate immunological responses. The in vitro data reported herein for the dendritic cells according to the invention indicate that these cells are useful as laboratory tools and also may have utility in the in vivo treatment of various diseases by adoptive immunotherapy, including cancer and viral infections.

The invention further relates to the use of TNF-$\alpha$ together with IL-3 or of GM-CSF to prepare a dendritic cell line or to induce dendritic cells; to the use of dendritic cells to generate $CD4^+$ helper T cells; to the use of $CD4^+$ helper T cells in adoptive immunotherapy; to the use of SCID-hu mice for human antibody production; and to the use of dendritic cells to generate cancer-specific and virus-specific $CD8^+$ cytotoxic T cells, especially to the use of dendritic cells to generate $CD8^+$ cytotoxic T cells specific against the AIDS virus.

A further feature of the invention comprises a mixed lymphocyte reaction comprising the steps of:

providing a sample of responder cells;

providing a sample of inactivated stimulator cells such that the stimulator cells are allogeneic with respect to the responder cells and such that the stimulator cells consist of dendritic cells produced by the process comprising the steps of (a) treating CD34$^+$ hematopoietic cells with TNF-$\alpha$ and IL-3 or with GM-CSF, and (b) isolating treated CD34$^+$ hematopoietic cells that express the CD1a antigen;

co-culturing the responder cells and the inactivated stimulator cells; and measuring a response of the responder cells.

DETAILED DESCRIPTION OF THE INVENTION

An important aspect of the invention is the generation of dendritic cells from CD34$^+$ hematopoietic cells. CD34$^+$ hematopoietic progenitor cells can be obtained from a variety of tissue sources, e.g. bone marrow, but are preferably obtained from umbilical cord blood samples as follows: Light-density mononuclear cells from the samples are isolated by Ficoll-Hypaque gradient separation (d=1.077 g/mL) and are depleted of adherent cells, e.g. by overnight incubation at 37° C. in RPMI 1640 medium supplemented with 1% w/v tissue-culture grade bovine serum albumin. Preferably, cells bearing CD34 antigen are isolated from non-adherent mononuclear fractions through positive selection by indirect immune panning using anti-CD34 monoclonal antibody, e.g. IMN-133.3 available from Immunotech (Marseille, France), ANTI-MY 10 available from Becton Dickinson (Mountain View, Calif.), or the like. Panning flasks are prepared as follows: sheep Fab antimouse IgG at a concentration of 25 µg/mL in Tris buffer (0.05 mol/L, pH 9.4) is distributed (10 mL) in 75-cm$^2$ tissue culture flasks for overnight coating at 4° C. Separately, the light-density mononuclear cells (depleted of adherent cells as discussed above) are incubated one hour at 4° C. with 5 µg/mL anti-CD34 antibody at 10$^7$ cells/mL in RPMI 1640 supplemented with 2% heat-inactivated pooled human AB serum (HABS). Afterwards, cells are washed in cold medium containing 2% HABS, and 10 mL containing about 5×10$^7$ cells are distributed to the flasks previously coated with sheep antimouse IgG, as described above. Following a two-hour incubation at 4° C., non-adherent cells in suspension (i.e. the CD34-depleted fraction) are harvested by gentle pipetting and rinsing several times with medium. The adherent "panned" cells (i.e. the CD34-rich fraction) are then recovered by vigorous pipetting.

The dendritic cells are obtained from the CD34$^+$ cells by culturing these in medium containing GM-CSF or TNF-$\alpha$ and IL-3. Preferably, the dendritic cells are obtained from the CD34$^+$ cells by culturing these in medium containing TNF-$\alpha$ as well as GM-CSF. TNF-$\alpha$, GM-CSF, and IL-3 suitable for use in the invention are commercially available, e.g. from Genzyme Corp. (Cambridge, Mass.), or can be produced by recombinant expression systems: e.g. as taught by Clark et al. in U.S. Pat. No. 4,959,455 (IL-3); Clark et al. in PCT application No. EP85/00326 (publ. no. WO86/00639) (GM-CSF); and Mark et al. in U.S. Pat. No. 4,677,063 (TNF-$\alpha$). Preferably, IL-3 and GM-CSF are used at saturating concentration; that is, they are used at a concentration at which all the IL-3 and GM-CSF receptors on the CD34$^+$ cells are occupied by biologically active IL-3 and GM-CSF molecules. Of course, the actual concentration may depend on the quality of IL-3 and GM-CSF used. Preferably, human IL-3 having a specific activity of at least 5×10$^6$ U/mg is employed, wherein a unit of activity corresponds to the half-maximum proliferative activity as determined by $^3$H-thymidine uptake by human bone marrow cells in liquid cultures. In the culture systems described below, saturating concentration was 10 ng/mL (or 50 U/mL). Preferably, human GM-CSF having a specific activity of at least 2×10$^6$ U/mg is employed, wherein a unit of activity is as defined for IL-3 above. In the culture systems described below, saturating concentration was 100 ng/mL (or 200 U/mL). Preferably, TNF-$\alpha$ is used at a concentration in the range of 2 to 3 ng/mL or 40–60 U/mL, most preferably at a concentration of about 2.5 ng/mL or 50 U/mL. Units of TNF-$\alpha$ are defined by Carswell et al., *Proc. Natl. Acad. Sci.*, Vol. 72, pg. 3666 (1975), and by Aggarwal et al., *J. Biol. Chem.*, Vol. 260, pg. 2345 (1985). The cells can be co-cultured in standard tissue culture medium with standard additives, such as RPMI 1640 supplemented with 10% (v/v) heat inactivated fetal bovine serum, 10 mM Hepes, 2 mM L-glutamine, 5×10$^{-5}$ M 2-mercaptoethanol, penicillin (100 U/mL) and streptomycin (100 mg/mL). Preferably, the CD34$^+$ cells are cultured in the presence of the cytokines for from 8 to 12 days.

Dendritic cells that form in the culture are isolated by panning as described above, with the exception that anti-CD1a and/or anti-CD14 antibodies are employed (both antibodies being commercially available, e.g. from Becton-Dickinson).

The MLR method of the invention comprises the following steps: (1) providing a sample of responder cells; (2) providing a sample of inactivated stimulator cells such that the stimulator cells are allogeneic with respect to the responder cells and such that the stimulator cells consist of dendritic cells produced by the process comprising the steps of (a) treating CD34$^+$ hematopoietic cells with TNF-$\alpha$ and IL-3 or with GM-CSF, and (b) isolating treated CD34$^+$ hematopoietic cells that express the CD1a antigen; (3) co-culturing the responder cells and the inactivated stimulator cells; and (4) measuring a response of the responder cells.

Preferably, the sample of responder cells consists of CD4$^+$ T cells from the peripheral blood of a patient who is to be the recipient of a transplant. Obtaining T cell populations employs techniques well known in the art which are fully described by DiSabato et al., eds., in *Meth. in Enzymol.*, Vol. 108 (1984). For example, the CD4$^+$ T cells can be isolated as follows: first mononuclear cells are isolated from the peripheral blood and depleted of adherent cells; CD4$^+$ T cells are then purified by depleting other cell types, for example by immunomagnetic depletion (e.g. with DYNABEADS, Dynal, Oslo, Norway), or the like, using a cocktail of commercially available monoclonal antibodies, e.g. anti-CD14, anti-CD16, anti-CD20, anti-CD8, anti- CD40 (available from Becton-Dickinson and/or Ortho Diagnostic Systems, New Jersey). CD4$^+$ populations having higher than 95% purity are typically achieved after two rounds of immunomagnetic depletion.

Stimulator cells of the invention are dendritic cells derived from CD34$^+$ hematopoietic progenitors cells obtained from a different person from that from whom the responder cells are taken; that is, the stimulator cells are allogeneic with respect to the responder cells. These cells are obtained as described above.

The stimulator cells of the invention are inactivated so that they can still carry out their stimulatory function but are inhibited from any other function that could obscure the response measured from the responder cells. Thus, the nature of the inactivation depends somewhat on the "read-out" of the assay. Preferably, the read-out, or response measured in the responder cells, is cellular proliferation. Other read-outs could also include such phenomena as cytokine production, cytolytic ability, and the like. Preferably, the stimulator cells are treated so that they are incapable of replication, but their antigen-processing machinery remains functional. This is conveniently accomplished by irradiating the cells, e.g. with about 1500 to 5000 R (gamma or X-radiation), preferably 3000 to 4000 R, before mixing with the responder cells.

Preferably, proliferation of the responder cells is determined by the uptake of tritiated thymidine using standard protocols. For example, from 10 to $2.5\times10^4$ stimulator cells are added to $2.4\times10^4$ allogeneic CD4$^+$ T cells in 96-well round-bottom tissue-culture plates and are incubated for 4 days in the medium described above. After incubation, the cells are pulsed with 1 $\mu$Ci of tritiated thymidine for 6 hours, and then they are harvested and measured for tritiated thymidine uptake, e.g. by scintillation counting.

EXPERIMENTAL

The following examples serve to illustrate the present invention. Cell lines, reagents and their concentrations, temperatures, and the values of other variables are only to exemplify the application of the present invention and are not to be considered limitations thereof.

EXAMPLE 1

Generation of Human Dendritic Cells

Figure 1A:
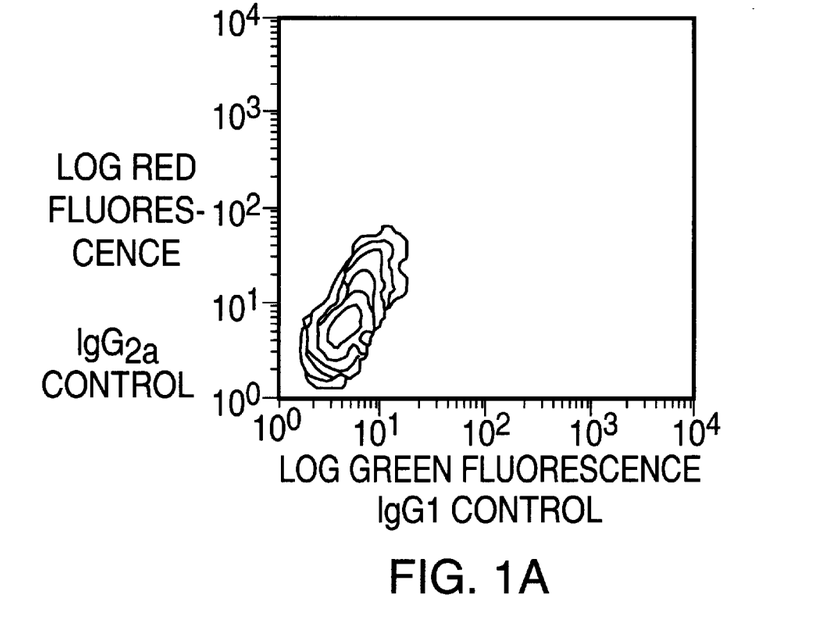
FIGS. 1A and 1B illustrate flow cytometry data showing the partial co-expression of CD14 by CD1a$^+$ cells.
Figure 1B:
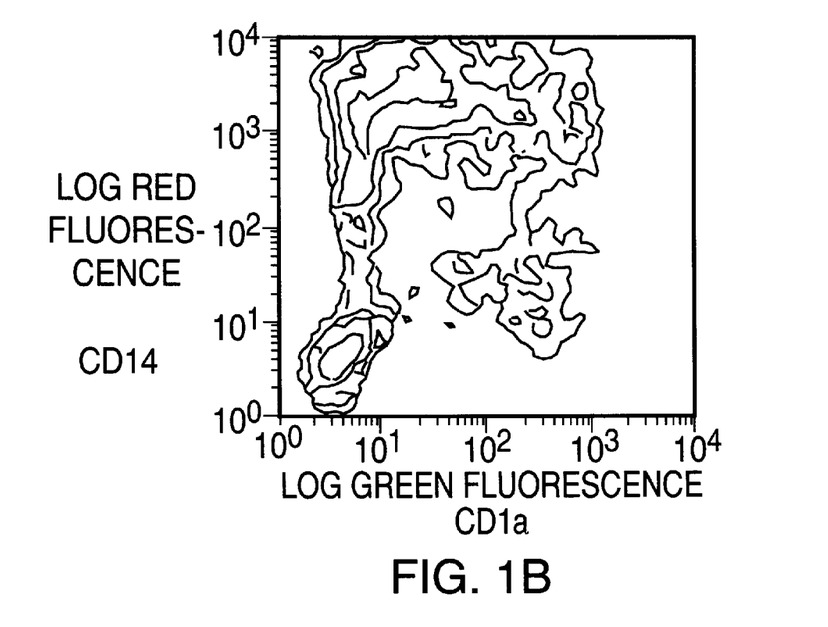
Figure 2A:
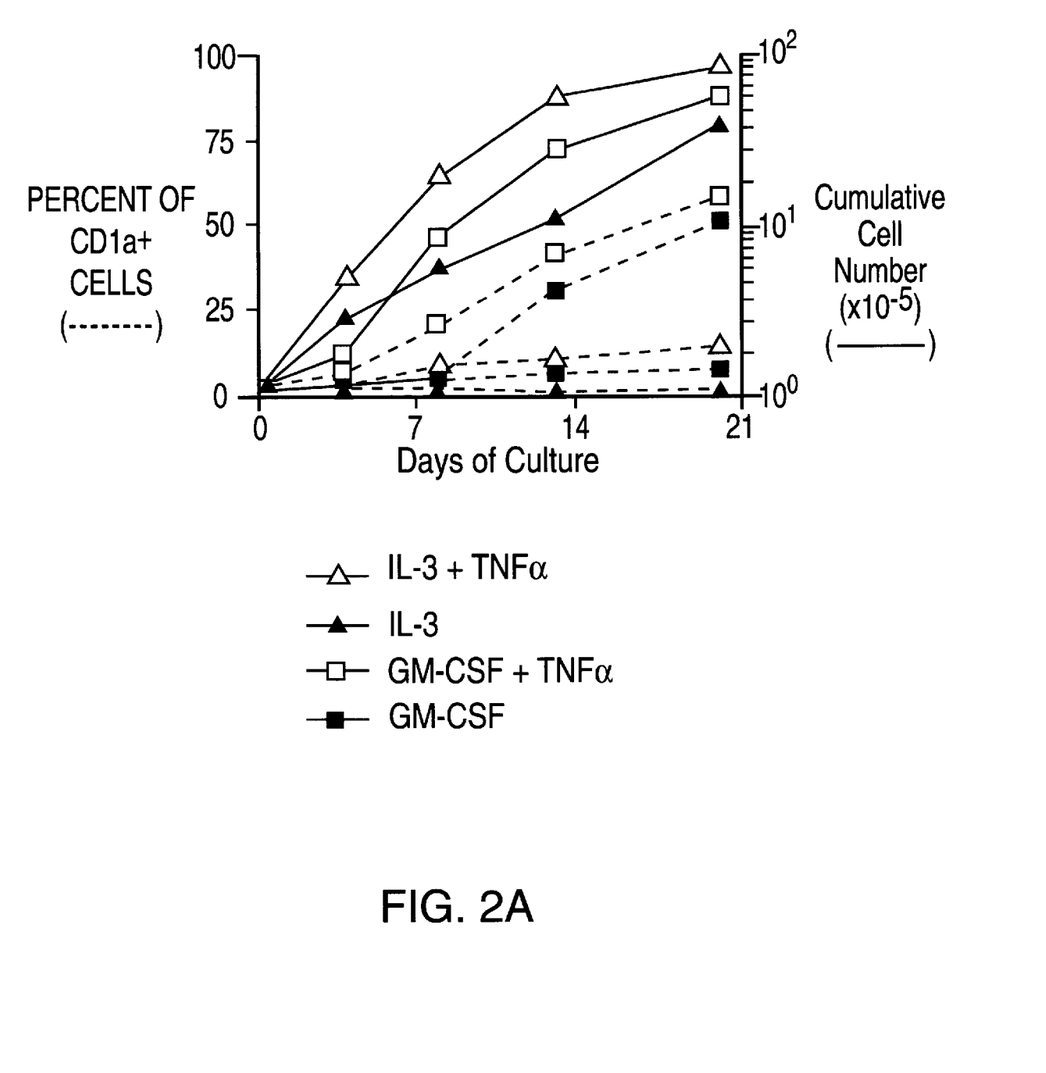
FIGS. 2A and 2B illustrates data concerning the growth kinetics of CD1a$^+$ cells under various medium conditions.
Figure 2B:
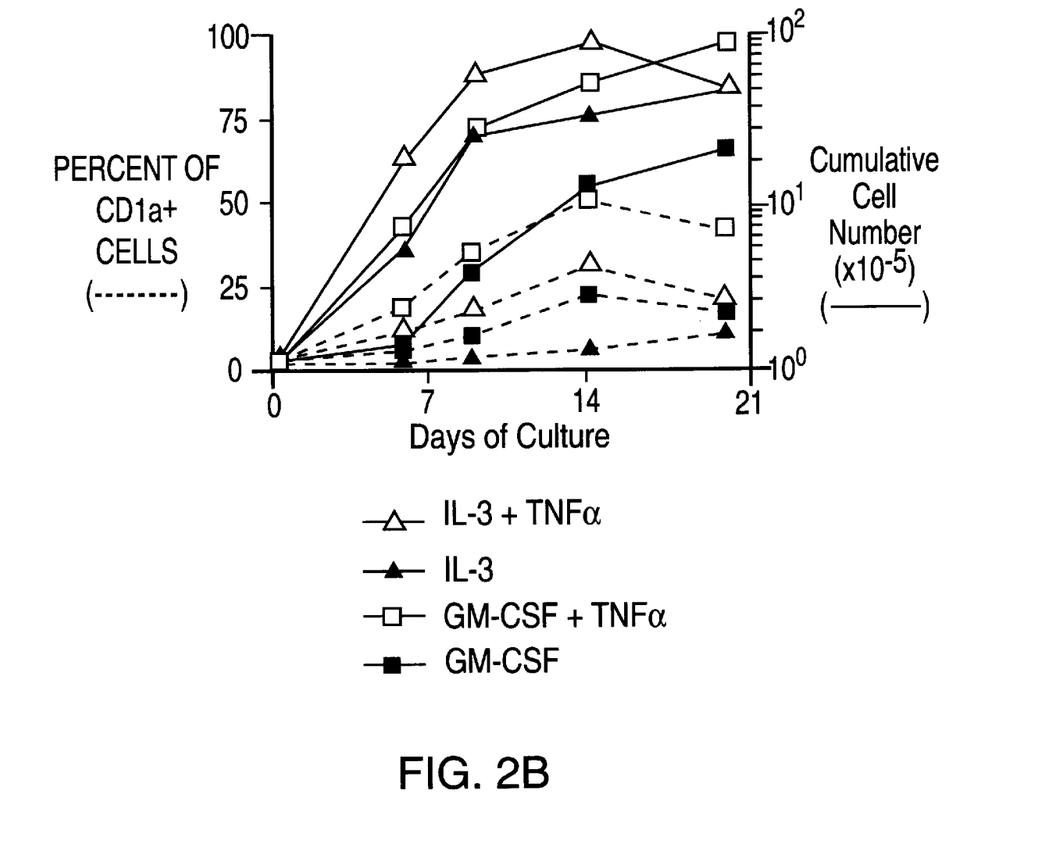

After 12 days of culture in GM-CSF and TNF-α, cells generated from CD34$^+$ cord blood hematopoietic precursor cells were processed for two-color fluorescence measurement. Briefly, cells were sequentially incubated with unconjugated monoclonal antibodies, phycoerythrin-conjugated (PE-conjugated) anti-mouse immunoglobulin, normal mouse serum, and monoclonal antibodies OKT6 (anti-CD1a from Ortho) or Leu-M3 (anti-CD14 from Becton-Dickinson), the monoclonal antibodies being directly labelled with fluorescein isothiocyanate (FITC). As shown in FIG. 1, culturing CD34$^+$ cells for 12 days in the presence of GM-CSF and TNF-α allows the appearance of CD14$^+$ monocytic cells co-expressing the CD1a antigen. In addition, a population of CD14$^-$CD1a$^+$ cells was consistently observed which represented 30–90% of the total CD1a population (range from 5 experiments). Within the monocytic lineage, expression of CD1a antigen is restricted to Langerhans cells. FIG. 1A shows two-color fluorescence intensity from IgG$_1$-FITC isotype control versus IgG$_{2a}$-PE isotype control. FIG. 1B shows two-color fluorescence intensity from OKT6-FITC (proportional to CD1a expression) versus Leu-M3-PE (proportional to CD14 expression). As shown in FIG. 2, CD1a$^+$ cells were not detected at the onset of the culture and the CD1a antigen could first be observed after 4 days of culture in the presence of TNF-α, and expression increased until day 20. Whereas less than 5% of CD1a$^+$ cells were observed in the presence of IL-3, 5–15% CD1a$^+$ cells were detected in GM-CSF. A large proportion of CD1a$^+$ cells were detected in IL-3 and TNF-α (10–25%) and mainly in GM-CSF and TNF-α (20–60%) (range of 5 experiments after 12 days of culture). In terms of growth efficiency, IL-3 plus TNF-α is 2–3 times more potent than IL-3 alone, and GM-CSF plus TNF-α is 3–4 times more potent than GM-CSF alone (FIG. 2). Thus, starting from 10$^5$ CD34$^+$ cells, after 12 days in culture, GM-CSF allowed the generation of 1–3×10$^6$ CD1a$^+$ cells, whereas in IL-3 plus TNF-α and GM-CSF plus TNF-α cultures of 2–3×10$^6$ cells were recovered. As GM-CSF plus TNF-α appeared to be the most potent combination of factors for generating CD1a$^+$ cells, all the cultures for the characterization of those cells contained GM-CSF plus TNF-α: FIG. 2 shows the expansion of 10$^5$ CD34$^+$ cells (i) in the presence of IL-3 (solid triangles), (ii) IL-3 and TNF-α (open triangles), (iii) GM-CSF (solid squares), and (iv) GM-CSF and TNF-α (open squares). Solid lines indicate total cell numbers in the three experiments, and dashed lines indicated expression of CD1a antigen. FIGS. 2A and 2B represent data from two separate sets of experiments.

The morphology of the CD1a$^+$ cells generated by the method of the invention was studied using both light and electron microscopy. Adherent cells observed in GM-CSF alone display the classical aspect of regularly shaped macrophages, whereas those obtained in the presence of GM-CSF plus TNF-α have a typical aspect of dendritic cells with highly ramified dendrites, lobulated nucleus, and a villous surface with dendritic projections. Some of the CD1a$^+$ cells (about 1 in 5) possess organelles with double membrane joining, recalling the structure of Birbeck granules.

The phenotype of CD1a$^+$ cells generated after 12 days of culture in the presence of GM-CSF and TNF-α was determined by two-color fluorescence analysis. Depending on the experiment, the percentage of CD1a$^+$ cells co-expressing CD14 varied between 10 and 70%. The results presented in Table I below were obtained from experiments in which less than 15% of CD1a$^+$ cells co-expressed CD14; thus, both CD1a$^+$ cells and CD1a$^-$CD14$^+$ cells were characterized. CD1a$^+$ cells co-expressed CD1c, CD4, and CD40, but did not express CD1b. In contrast, CD1a$^-$CD14$^+$ cells did not express CD1c and only weakly expressed CD4 and CD40. Both CD1a$^+$ and CD14$^+$ cells were found to bear FcγRII (CD32), FcγRIII (CD16), and CR3 (CD11b), whereas only CD1a$^-$CD14$^+$ cells expressed FcγRI (CD64) and CR1 (CD35). CD1a$^+$ and CD1a$^-$CD14$^+$ cells expressed both LFA1α (CD11a) and LFA1β (CD18), but CD1a$^+$ cells exhibited higher levels of ICAM1 (CD54) than CD1a$^+$ CD14$^+$ cells. CD1a$^+$ cells expressed very high levels of HLA-DR (5–10 times more than CD14$^+$ cells). In contrast, CD1a$^-$CD14$^+$ cells expressed high levels of HLA-DQ$^+$.

TABLE I

Phenotype of Dendritic Cells of the Invention

| Antigen | Antibody | Reactivity with CD1a cells | Reactivity with CD14 cells | Source of Antibody (*) |
|---|---|---|---|---|
| CD1a | OKT6, IOT6a, T6, DMC1, L544 | ++ | − | Ort, Hy8, Imu, Cou, |
| CD1b | IOT6b | − | − | Imu |
| CD1c | IOT6c | + | − | Imu |
| CD14 | Leu-M3 | +/− | +++ | BD |
| CD4 | IOT4 | ++ | +/− | Imu |
| CD40 | Mab 89 | ++ | +/− | EP |
| CD16 | Leu11b | + | + | BD |
| CD32 | 2E1 | +/− | +/− | Imu |
| CD64 | 197 | − | + | Med |
| CD21 | CR2 | − | − | BD |
| CD11b | IOM1 | ++ | ++ | Imu |
| CD35 | IOT17 | − | ++ | Imu |
| CD54 | 84H10 | +++ | + | Imu |
| CD11a | SPVL7 | ++ | ++ | Hy2 |
| CD18 | BL5 | ++ | ++ | Imu |
| HLA-DR | L243 | ++++ | ++ | BD |
| HLA-DQ | SPVL3 | +++ | + | Imu |

*Antibodies were obtained from sources as follows: Ort = Ortho Diagnostic Systems; Imu = Immunotech; Cou = Coulter (Hialeah, FL); BD = Becton-Dickinson; Med = Medarex Inc. (Lebanon, NH); Hy2 = Hybridoma, Vol. 2, pg. 423 (1983); Hy8 = Hybridoma, Vol. 8, pg. 199 (1989); EP = Eur. Pat. Appl. 89 403 491.7

EXAMPLE 2

Proliferation of CD4$^+$ T Cells after Stimulation by Dendritic Cells

CD34$^+$ cells were cultured for 12 hours in accordance with the invention, after which they were irradiated with 4000 Rads to form stimulator cells for the experiment. From 10 to (2.4×10$^4$) stimulator cells were seeded for 2.5×10$^4$ resting CD4$^+$ T cells or other responder cells in round-bottomed microtest tissue culture plates in medium supplemented with 10% human AB$^+$ serum, as described below.

Figure 3A:
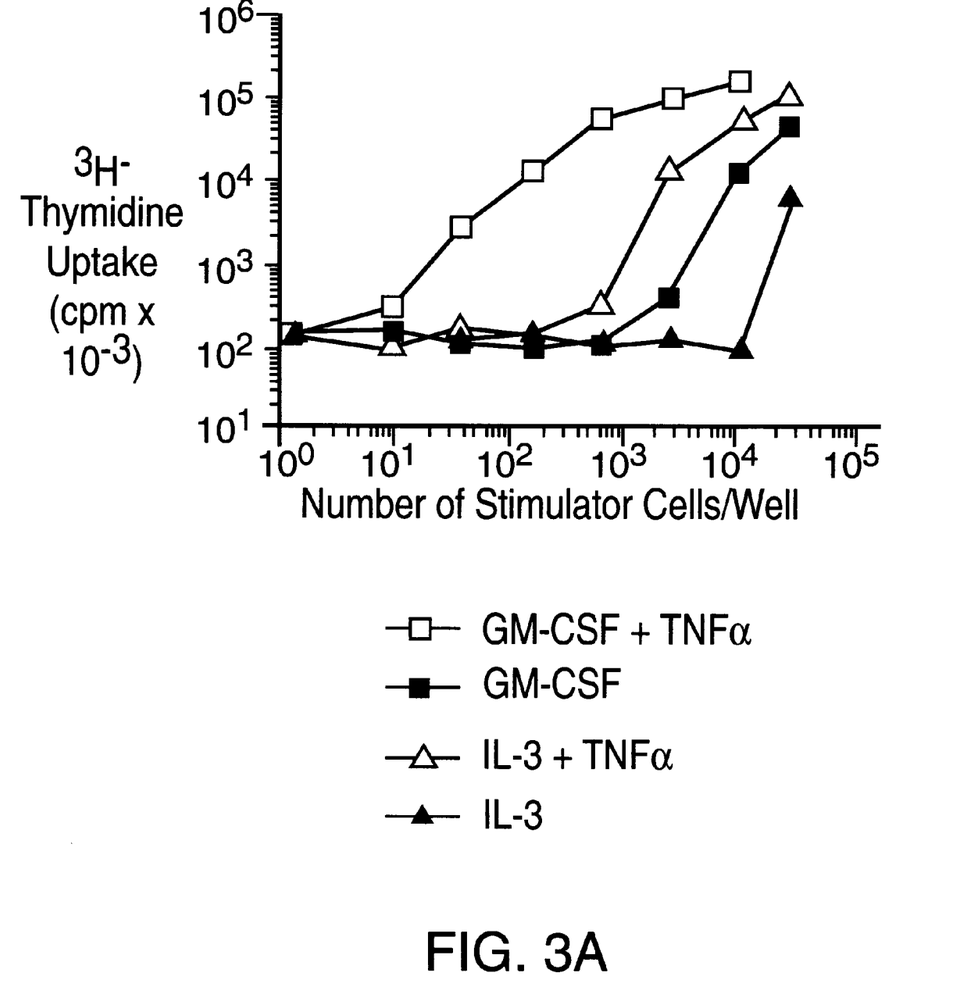
FIGS. 3A and 3B illustrates data of CD4$^+$ cell proliferation after stimulation by dendritic cells of the invention.

Dendritic cells of the invention were assayed for their capacity to induce resting allogeneic CD4$^+$ T cells (as responder cells) to proliferate. As shown in FIG. 3A, cells cultured in the presence of IL-3 alone (solid triangles) induced marginal allogeneic CD4$^+$ T cell proliferation. In contrast, cells cultured in the presence of GM-CSF alone (solid squares), in the presence of IL-3 plus TNF-α (open triangles), and in the presence of GM-CSF plus TNF-α (open squares), induced a strong proliferation of allogeneic CD4$^+$ T cells. Depending on culture conditions of the CD34$^+$ progenitor cells, the optimal proliferation of the CD34$^+$ T cells was observed for different values of the ratio (stimulator cells)/(allogeneic CD34$^+$ T cells). In comparison with control values (CD34$^+$ T cells without stimulator cells), a 50-fold enhancement of tritiated thymidine uptake by CD4$^+$ T cells was observed at a ratio of 1:3.8 (range 1:3 to 1:25), 1:12.5 (range 1:10 to 1:35), and 1:360 (range 1:100 to 1:400) for cells cultured in the presence of GM-CSF alone, IL-3 plus TNF-α, and GM-CSF plus TNF-α respectively (ranges from 5 experiments).

Figure 3B:
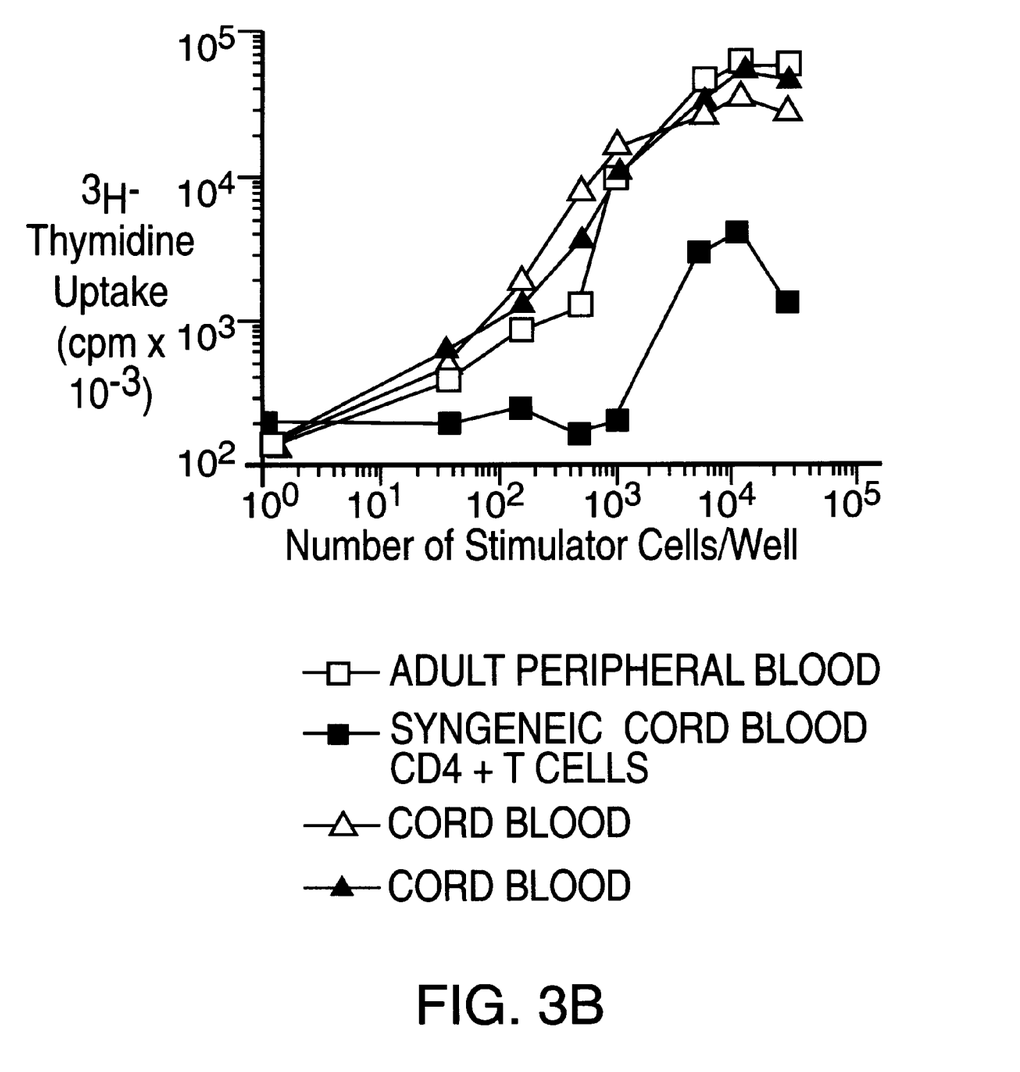

In the Experiment illustrated in FIG. 3B, the CD34$^+$ cells were cultured in the presence of GM-CSF and TNF-α for all experiments and the responder cells were adult peripheral blood (open squares), cord blood (open and solid triangles), and syngeneic cord blood CD4$^+$ T cells (solid squares). FIG. 3B shows that allogeneic CD4$^+$ T cells derived either from cord blood or from adult peripheral blood were equally stimulated, and that syngeneic CD4$^+$ T cells were stimulated to a much lower extent (response 20-fold weaker than allogeneic cells).

Figure 4:
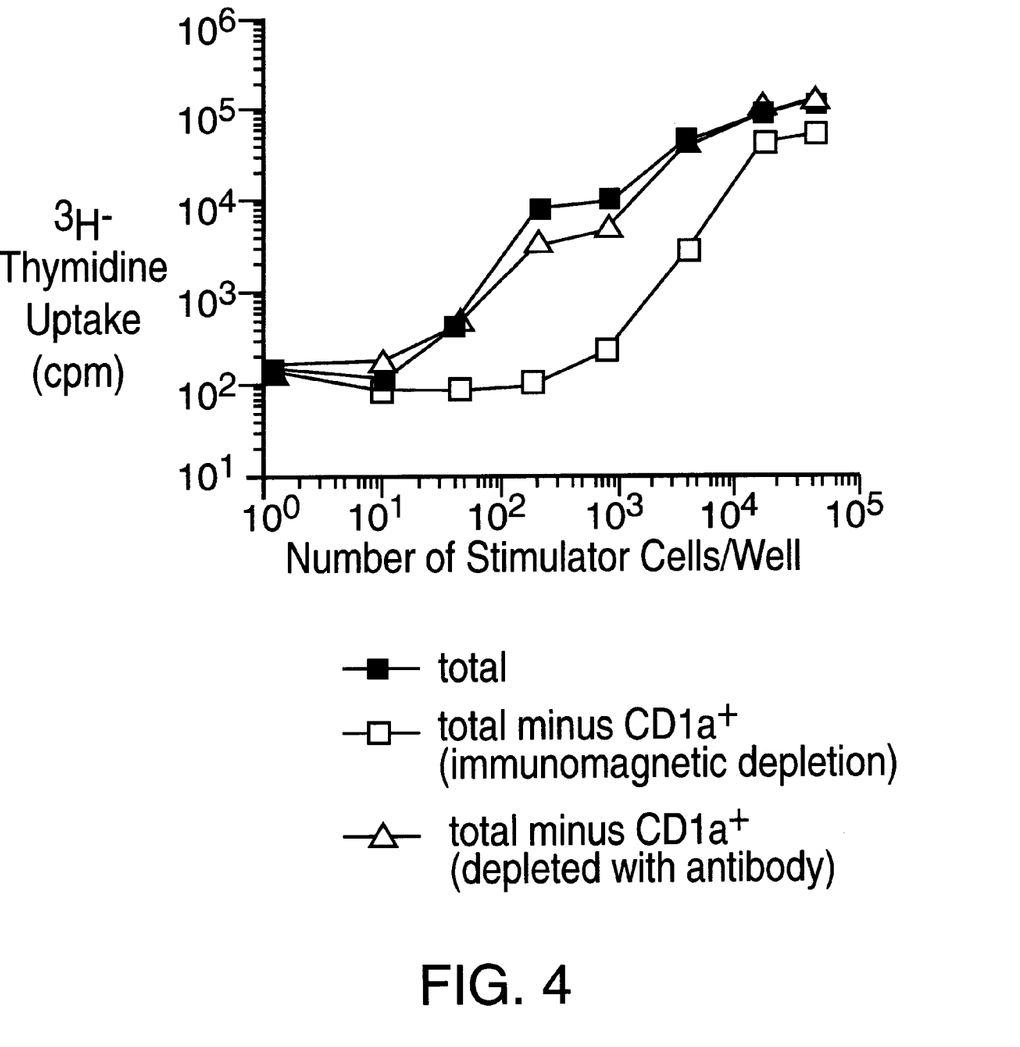
FIG. 4 illustrates data showing the effect of CD1 a$^+$ cells in stimulation of allogeneic CD4$^+$ T cell proliferation.

When, after 12 days of culture in the presence of GM-CSF and TNFα, CD1a$^+$ cells were removed by immunomagnetic depletion (FIG. 4), a strong loss of induction capacity was observed. A 50-fold enhancement of CD4$^+$ T cell proliferation was observed for a ratio (stimulator cells)/(allogeneic CD4$^+$ T cells) of 1:200 (range of 3 experiments 1:200 to 1:400) and 1:8 (range of 3 experiments 1:8 to 1:40) before and after CD1a$^+$ cells were depleted, respectively. After irradiation, the following were used as stimulator cells: total population (solid squares), population from which CD1a$^+$ cells had been removed by depletion (open squares), and control population from which depletion was carried out with an anti-IgG$_1$ isotype antibody (open triangles).

EXAMPLE 3

Generation of Cancer-specific CD8 Cytotoxic T Cells for Adoptive Immunotherapy

CD34$^+$ cells are isolated from the peripheral blood of a cancer patient and grown in the presence of GM-CSF and TNF-α, as described above. Peripheral blood CD8 cells are cryopreserved. Once dendritic cells are generated, CD8 T cells are thawed and mixed with the patient's cancer cells. After sensitization, CD8 T cells are expanded in the presence of IL-2, e.g. as described by Rosenberg, U.S. Pat. No. 4,690,915. Total cells are reinfused into the patient provided that they display tumor-specific cytotoxic activity. The tumor cells may be replaced by specific tumor antigens, e.g. van der Bruggen et al., Science, Vol. 254, pp. 1643 (1991).

Dendritic Cells Generated in the Presence of GM-CSF and TNF-α are Strong Stimulators of Resting Allogeneic CD8$^+$ T Cell Proliferation Dendritic cells generated from CD34$^+$ cord blood progenitors were cultured for 12 days and irradiated (4000 Rads), and then were used as stimulator cells for resting CD4$^+$ and CD8$^+$ T cells. From 10 to 2.5×10$^3$ stimulator cells were seeded for 2×10$^4$ resting T cells, in round-bottomed microtest tissue-culture plates, in medium supplemented with 10% human AB$^+$ serum, with or without 20 U/ml IL-2. After 5 days' incubation, cells were pulsed with 1 µCi of $^3$H-thymidine for 8 hours, harvested and counted. Tests were carried out in triplicate and results were expressed as mean counts per minute.

Figure 5:
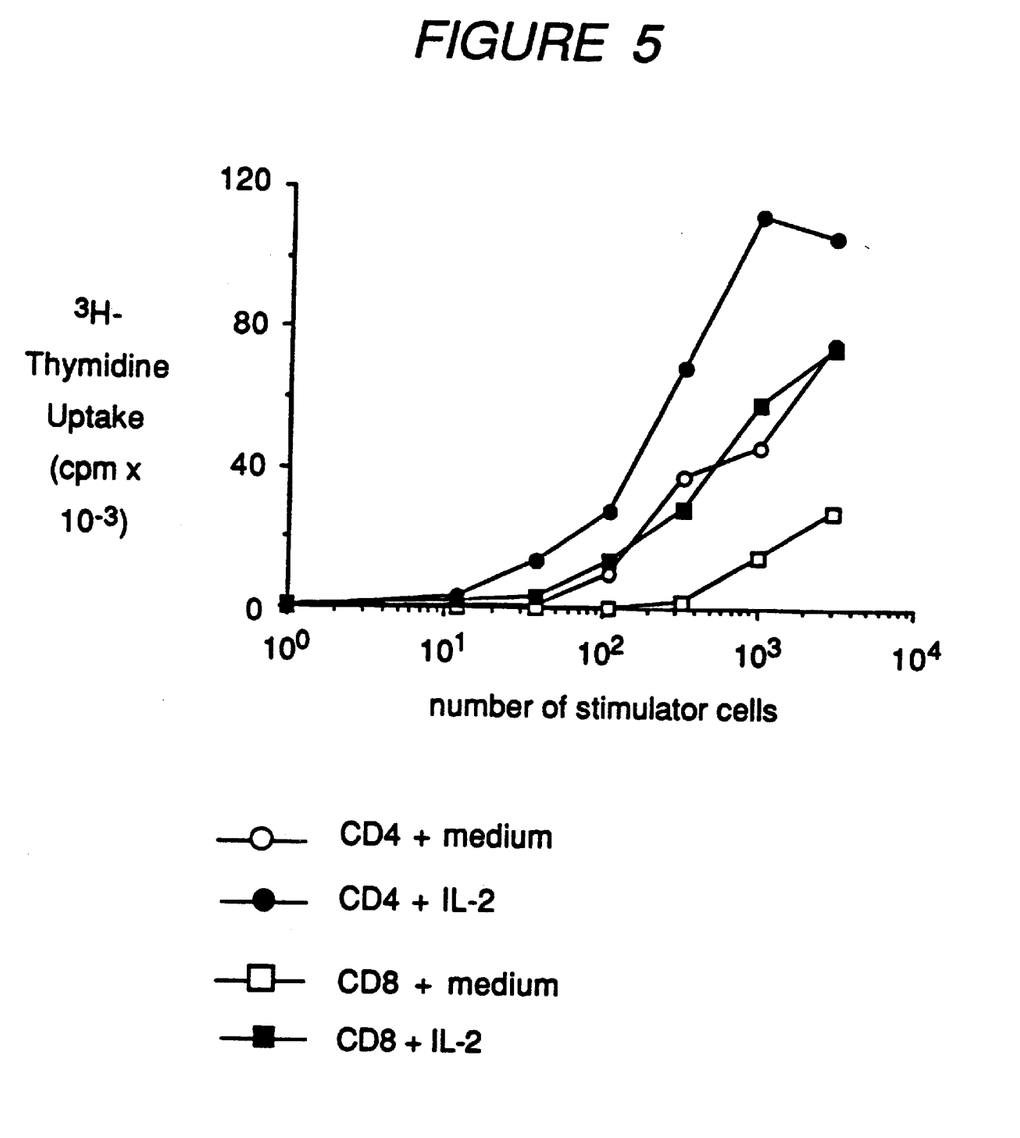
FIG. 5 illustrates data of CD4$^+$ and CD8$^+$ T cell proliferation after stimulation by dendritic cells of the invention.

The addition of IL-2 to the medium in which the CD4$^+$ and CD8$^+$ T cells were cultured indeed stimulated the proliferation of the CD4$^+$ and CD8$^+$ T cells, as shown by their $^3$H-thymidine uptake. As shown in FIG. 5, CD8$^+$ cells cultured in the presence of medium alone (open squares) showed very little proliferation whereas CD8$^+$ cells cultured in the presence of IL-2 (solid squares) showed much more proliferation; moreover, CD4$^+$ cells cultured in the presence of medium alone (open circles) showed little proliferation whereas CD4$^+$ cells cultured in the presence of IL-2 (solid circles) showed considerably more proliferation.

EXAMPLE 4

Generation of Primary and Secondary Antibody Responses in SCID-hu Mice

SCID-hu mice have allowed secondary responses to recall antigens but have not permitted the establishment of primary responses: e.g. Moller, The SCID-hu Mouse, Vol. 124

(Munksgaard, Copenhagen, 1991); Duchosal et al., *Nature*, Vol. 355, pp. 258 (1992); and Mosier et al., *Curr. Top. Microbiol. Immunol.*, Vol. 152, pp. 195 (1989). It is believed that this is due to a lack of reconstitution of the dendritic cell pool. As antigen-pulsed dendritic cells can efficiently induce an antibody response in vivo, e.g. Sornasse et al., *J. Exp. Med.*, Vol. 175, pp. 15 (1992), SCID-hu mice are reconstituted with the dendritic cells generated in vitro from the CD34 cells of the donor of human cells or from another donor sharing a compatible MHC. Dendritic cells are pulsed with the appropriate antigen prior to injection. Once the mouse displays antibody to the antigen, B cells are isolated from blood and other reconstituted organs and immortalized, e.g. by culturing in the CD40 system in the presence of Epstein-Barr virus as taught by Banchereau et al., *Science*, Vol. 251, pp. 70 (1991).

EXAMPLE 5

Treatment of AIDS by Adoptive Immunotherapy with Dendritic Cells Generated In Vitro Dendritic cells are infected by HIV in vitro and HIV is found budding from the surface of the cells after 3–5 days in culture with HIV: e.g. Patterson, *J. Gen. Virol.*, Vol. 68, pgs. 1177–1181 (1987); Macatonia et al., *Immunology*, Vol. 71, pgs. 38–45 (1990); and Knight et al., *Immunol. Lett.*, Vol. 19, pgs. 177–182 (1988). Evidence for in vivo infection of dendritic cells by HIV comes from the description of infection of Langerhans cells of the skin and reduction in the amount of MHC class II molecules in cells of the skin: e.g. Tschachler et al., *J. Invest. Dermatol.*, Vol. 88, pgs. 233–237 (1987); and Belsito et al., *N. Engl. J. Med.*, Vol. 310, pgs. 1279–1282 (1984). Furthermore, 3–21% of blood dendritic cells from HIV patients contain HIV, with a level of infection two orders of magnitude greater than that seen in other cell types: Macatonia et al., *Immunology*, Vol. 71, pgs. 38–45 (1990). The infection of dendritic cells by the virus blocks their ability to present antigen to T cells, and thus inhibits the recruitment/proliferation of the T cells which is necessary for a successful immune response.

$CD34^+$ cells of HIV patients are used to generate dendritic cells in accordance with the invention. The dendritic cells are then incubated with selected antigens and reinfused into the HIV patient.

What is claimed:

1. A process for generating cancer-specific or virus-specific $CD8^+$ cytotoxic T cells comprising:
    (a) removing $CD8^+$ T cells from a human patient; and
    (b) culturing the $CD8^+$ T cells with an amount of antigen-pulsed dendritic cells sufficient to sensitize and cause proliferation of $CD8^+$ cytotoxic T cells; wherein said dendritic cells are in vitro generated dendritic cells pulsed with a cancer or viral antigen.

2. The process of claim 1 wherein the patient's $CD8^+$ T cells are sensitized by mixing with the patient's cancer cells.

3. The process of claim 1 wherein the patient's $CD8^+$ T cells are sensitized with cancer antigens and cancer specific $CD8^+$ cytotoxic T cells are generated.

4. The process of claim 1 wherein the patient's $CD8^+$ T cells are sensitized with viral antigens and virus specific $CD8^+$ cytotoxic T cells are generated.

5. The process of claim 4 wherein the patient's $CD8^+$ T cells are sensitized with viral antigens of the AIDS virus and the resulting $CD8^+$ cytotoxic T cells are specific against the HIV virus.

6. A process of treating a patient suffering from cancer or a viral infection comprising:
    (a) removing $CD8^+$ T cells from a human patient;
    (b) culturing the $CD8^+$ T cells with an amount of antigen-pulsed dendritic cells sufficient to sensitize and cause proliferation of cancer-specific or virus-specific $CD8^+$ cytotoxic T cells, wherein said dendritic cells are in vitro generated dendritic cells pulsed with a cancer or viral antigen; and
    (c) returning the cancer-specific or virus-specific $CD8^+$ cytotoxic T cells to said patient.

* * * * *

UNITED STATES PATENT AND TRADEMARK OFFICE
CERTIFICATE OF CORRECTION

PATENT NO. : 6,004,807
DATED : December 21, 1999
INVENTOR(S) : Jacques Banchereau and Christophe Caux It is certified that error appears in the above-identified patent and that said Letters Patent is hereby corrected as shown below:

In the Title field, insert the phrase --AND USES THEREOF-- so that the full title reads "IN VITRO GENERATION OF HUMAN DENDRITIC CELLS AND USES THEREOF";

In the Inventors field, delete the word "Lyons" and insert therefor --Lyon--; and In the Foreign Application Priority Data field, insert --March 29, 1993 PCT PCT/US93/02639--.

Signed and Sealed this

Seventeenth Day of April, 2001

Attest:

NICHOLAS P. GODICI

Attesting Officer     Acting Director of the United States Patent and Trademark Office